(12) United States Patent
Obrebski et al.

(10) Patent No.: US 7,248,402 B2
(45) Date of Patent: Jul. 24, 2007

(54) SURGICAL MICROSCOPY SYSTEM

(75) Inventors: Andreas Obrebski, Düsseldorf (DE);
Günther Geiss, Konigsbronn (DE);
Klaus-Georg Knupfer, Essingen (DE);
Ludwin Monz, Mainz (DE); Lauric Weber, Aalen (DE); Gerhard Gaida, Aalen (DE); Martin Kraus, Hüttlingen (DE)

(73) Assignee: Carl Zeiss Surgical GmbH, Oberkochen (DE)

( * ) Notice: Subject to any disclaimer, the term of this patent is extended or adjusted under 35 U.S.C. 154(b) by 157 days.

(21) Appl. No.: 10/730,021

(22) Filed: Dec. 9, 2003

(65) Prior Publication Data

US 2005/0057800 A1 Mar. 17, 2005

(30) Foreign Application Priority Data

Dec. 9, 2002 (DE) ................. 102 57 452
Oct. 8, 2003 (DE) ................. 103 46 639

(51) Int. Cl.
*G02B 21/00* (2006.01)
*G02B 21/06* (2006.01)

(52) U.S. Cl. .............. 359/368; 359/385; 359/390
(58) Field of Classification Search ........ 359/368–390; 362/216, 551
See application file for complete search history.

(56) References Cited

U.S. PATENT DOCUMENTS

| | | | | |
|---|---|---|---|---|
| 3,776,614 A | * | 12/1973 | Kloots et al. | 359/376 |
| 4,291,938 A | * | 9/1981 | Wagner | 359/387 |
| 4,321,917 A | * | 3/1982 | Campbell | 128/205.26 |
| 4,523,732 A | | 6/1985 | Biber et al. | 248/123.11 |
| 4,818,085 A | * | 4/1989 | Schindl et al. | 359/390 |
| 4,912,388 A | * | 3/1990 | Tanaka et al. | 318/640 |
| 5,048,941 A | | 9/1991 | Hamada et al. | 359/368 |
| 5,074,651 A | * | 12/1991 | Nagamine | 359/384 |
| 5,288,987 A | | 2/1994 | Vry et al. | 250/201.3 |
| 5,309,277 A | * | 5/1994 | Deck | 359/387 |
| 5,312,393 A | | 5/1994 | Mastel | 606/4 |
| 5,325,231 A | * | 6/1994 | Tamura et al. | 359/387 |
| 5,667,186 A | | 9/1997 | Luber et al. | 248/550 |
| 5,757,193 A | * | 5/1998 | Yu et al. | 324/501 |
| 5,790,307 A | | 8/1998 | Mick et al. | 359/382 |

(Continued)

FOREIGN PATENT DOCUMENTS

DE 39 33 343 A1 4/1990

(Continued)

OTHER PUBLICATIONS

Combitrans— Kontaktiose Drehubertrager fur Energie Und Daten, Catalog for MST Aerospace GmbH, pp. 1-24 [with translation of revlevant sections on pp. 3-5].

*Primary Examiner*—Thong Q Nguyen
(74) *Attorney, Agent, or Firm*—Potomac Patent Group PLLC

(57) ABSTRACT

The present invention relates to a surgical microscopy system, comprising a surgical microscope, a stand comprising a base and a plurality of pivotally connected arms, the surgical microscope being mounted to one of the arms, wherein the pivotally connected arms are arranged to be movable with respect to each other such that the surgical microscope is movable relative to the base, and wherein a conventionally provided lead is replaced by one or more leads fulfilling the function of the single lead together. The present invention also relates to a surgical microscopy system, wherein data or/and energy is transmitted to the surgical microscope by wireless transmission.

13 Claims, 5 Drawing Sheets

U.S. PATENT DOCUMENTS

| | | |
|---|---|---|
| 5,803,579 A | 9/1998 | Turnbull et al. ............. 362/516 |
| 5,805,335 A | 9/1998 | Fukaya et al. ............... 359/384 |
| 5,820,250 A * | 10/1998 | Betts et al. .................. 362/216 |
| 5,945,744 A | 8/1999 | Dobler et al. .............. 307/10.1 |
| 6,150,666 A | 11/2000 | Engelhardt et al. .... 250/559.22 |
| 6,155,975 A | 12/2000 | Urich et al. ................. 600/300 |
| 6,213,943 B1 | 4/2001 | Abreu ......................... 600/405 |
| 6,217,188 B1 | 4/2001 | Wainwright et al. ........ 362/103 |
| 6,238,076 B1 | 5/2001 | Pascale et al. .............. 362/558 |
| 6,300,923 B1 | 10/2001 | Havel .......................... 345/83 |
| 6,305,659 B1 | 10/2001 | Metelski ..................... 248/519 |
| 6,392,794 B1 | 5/2002 | Engelhardt et al. ......... 359/368 |
| 6,394,999 B1 | 5/2002 | Williams et al. ............... 606/5 |
| 6,461,030 B1 * | 10/2002 | Shimokawa et al. ........ 362/551 |
| 6,493,134 B2 | 12/2002 | Pensel ........................ 359/388 |
| 6,650,703 B1 | 11/2003 | Schwarzmann et al. ..................... 375/240.01 |
| 2001/0044577 A1 | 11/2001 | Braun et al. ................. 600/417 |
| 2001/0055061 A1 | 12/2001 | Onishi et al. ................. 348/65 |
| 2002/0125061 A1 | 9/2002 | Kawamura .................. 180/400 |
| 2003/0137723 A1 | 7/2003 | Sander ........................ 359/380 |

FOREIGN PATENT DOCUMENTS

| | | |
|---|---|---|
| DE | 40 34 578 A1 | 5/1992 |
| DE | 41 31 737 A1 | 3/1993 |
| DE | 43 20 443 C2 | 12/1994 |
| DE | 43 34 069 A1 | 4/1995 |
| DE | 196 33 997 C1 | 3/1998 |
| DE | 697 08 334 T2 | 4/1998 |
| DE | 196 50 391 C2 | 6/1998 |
| DE | 199 27 724 A1 | 1/2000 |
| DE | 199 44 148 A1 | 3/2001 |
| DE | 100 03 269 A1 | 8/2001 |
| DE | 102 09 539 A1 | 9/2002 |
| DE | 102 02 125 A1 | 7/2003 |
| EP | 0 048 404 B1 | 3/1982 |
| EP | 0 656 194 B1 | 6/1995 |
| EP | 1 124 150 A1 | 8/2001 |
| GB | 2 338 568 A | 12/1999 |
| WO | WO 97/07487 | 2/1997 |
| WO | WO 98/13716 | 4/1998 |

* cited by examiner

SURGICAL MICROSCOPY SYSTEM

This application claims the benefit of priority applications DE 102 57 452.9 filed in Germany on Dec. 9, 2002 and DE 103 46 639.8 filed in Germany on Oct. 8, 2003. The subject matter of both of these applications is incorporated herein by reference.

BACKGROUND OF THE INVENTION

1. Field of the Invention

The present invention relates to a surgical microscopy system comprising a surgical microscope and a stand for the surgical microscope.

The surgical microscope can be used by a surgeon to obtain an enlarged image of a field for surgery during surgery. The stand comprises, starting from a base of the stand, a plurality of pivotally connected arms of the stand, onto one of which the surgical microscope is mounted. The arms are movable with respect to one another, for instance by pivoting, so as to change a spatial position of the surgical microscope relative to that of the base and, thus, relative to the field for surgery. In order to take some strain off the surgeon and in order to enable a spatial positioning of the surgical microscope to be as precise as possible, the stand comprises means for balancing the surgical microscope such that substantially independent of the position of the surgical microscope relative to the base, smallest possible forces need to be exerted onto the surgical microscope or one of the arms of the stand in order to spatially move the surgical microscope.

2. Brief Description of Related Art

Examples of a mechanical construction of such balanced stands are known, for instance, from German laid-open patent applications DE 43 20 443 A1 or DE 43 34 069 A1.

Apart from the mechanical function of holding the surgical microscope above the field for surgery, the stand also functions to guide various leads necessary in an operation of the surgical microscope along at least a part of the arms of the stand to the surgical microscope. These "leads" comprise, for instance, electrical wires for supplying driving power to a power consumer comprised in the surgical microscope. Examples of such power consumers are a motor operator for operating a zoom system of an optical arrangement of the surgical microscope, a data acquisition system, such as a camera or a distance metering system, and a data display unit for feeding data and images to be viewed by the surgeon into an optical path of the optical arrangement of the surgical microscope. These "leads" further comprise data lines for supplying data acquired by the data acquisition system, for instance, to a data recording system or a data processing system disposed, respectively, at a distance from the surgical microscope und, additionally, for transmitting data to the surgical microscope, for instance for being displayed to the surgeon by means of the data display system.

Further more, the "leads" also comprise light guides, in order to guide light required to illuminate the field for surgery to the same. The light source for this light is conventionally disposed on the base of the stand and light emitted by the light source coupled into a light guide and led along the arms of the stand to the surgical microscope and emitted by the surgical microscope in a direction of an object plane of the surgical microscope.

However, even carefully balanced stands have turned out to have disadvantages for the surgeon during practical use in that remaining forces of the stand tend to move the surgical microscope into one direction or the other.

In particular, it has turned out that the stand, even if it is satisfactorily balanced out for one position of the surgical microscope, still develops remaining forces in a different position of the surgical microscope.

It is therefore an object of the present invention to provide a surgical microscopy system comprising a stand having improved balancing.

For achieving this object, means are provided which dispose of the need to guide leads of one or another kind along at least some of the arms.

The inventors found that the remaining forces referred to above are generated by those leads and that these remaining forces are eventually generated by a local distortion of the leads in those areas where the leads extend from one arm of the stand to the next. Due to the displacement of the arms of the stand relative to one another, these distortions change and, thus, the remaining forces generated by these leads change. This is also the reason why they cannot be compensated for in substantially all spatial positions of the surgical microscope by balancing.

In order to put the concept of the present invention of reducing the remaining forces attributable to the leads into practice, one embodiment of the present invention involves replacing a conventional lead of little flexibility by a more flexible lead, and, in particular, replacing a conventional lead of a given thickness and stiffness by two separate leads of decreased overall thickness and stiffness.

Further more, an embodiment is provided wherein a transmission by means of a lead is replaced by a wireless transmission by an emitter disposed at a distance from the surgical microscope directly to a receiver disposed at the surgical microscope or from an emitter disposed on the surgical microscope to a receiver disposed at a distance from the surgical microscope.

The embodiments of the present invention described in the following have in common that they comprise a surgical microscope and a stand having a base and a plurality of pivotally connected arms, the surgical microscope mounted to one of the arms, wherein the pivotally connected arms are arranged to be movable with respect to each other such that the surgical microscope is movable relative to the base.

A base of the stand may be a footing of the stand placed on the floor of a room. The base of the stand may, however, also be a fixing attachment for fixing the stand to a ceiling or a wall of the room or any other object, such as a further stand.

In one embodiment of the present invention a light emitter for illuminating a field for surgery is provided on the surgical microscope, and the surgical microscopy system comprises a light guiding system for supplying light to the light emitter. Herein, at least two separate light guides are provided, which guide the light together to a single light emitter. It has turned out that a light guide with a given light guiding diameter has a larger stiffness than two light guides with only half the given diameter each combined. The at least two light guides are supported on at least one pair of pivotally connected arms of the stand and are attached to each arm of the pair at an attachment position on the respective arm, wherein the two attachment positions are disposed at a distance from each other. The at least two separate light guides still exert remaining forces depending on a position from the position of the pair of arms of the stand in relation to one another, these remaining forces, however, are generally lower than the remaining forces exerted by a conventionally used single light guide.

A further embodiment provides a light source for supplying light to the light emitters, which light source is disposed directly on the surgical microscope. Such an approach has not been taken so far since powerful illumination systems for surgical microscopes make use of light guides, for the supply of light throughout. Disposing the source of light directly on the surgical microscope increases the weight thereof and is thus associated with a certain disadvantage. This disadvantage, however, is more than compensated for by the fact that the remaining forces conventionally created by the light guide are avoided due to the ability of the stand to balance out the higher weight of the surgical microscope.

In an exemplary embodiment, a semiconductor device such as a light emitting diode is used as the light source. The inventors have found that modern semiconductor devices are capable of producing a comparatively high output, which, surprisingly, is sufficient to illuminate a field for surgery in practice to a satisfactory extend. Accordingly, the inventors deviated from the approach laid out by the state of the art, i.e. supply of increasing light output to the surgical microscope by means of ever thicker light guides. In contrast, they have proposed an entirely different solution as compared to this conventional approach, in particular arranging the light source in the form of a semiconductor device on the surgical microscope itself.

In an exemplary embodiment, for generating electrical power (in particular current) and for supplying electrical power (current) to the light emitter or light source, respectively, at least one electrochemical cell disposed on the surgical microscope is provided, such as one of a battery, an accumulator and a fuel cell. This makes it possible to avoid a power supply lead for the light source extending along the arms of the stand.

A further embodiment provides two independent electrochemical cells on the surgical microscope, wherein only one of the cells is sufficient to enable operation of the surgical microscope, which means, herein in particular, the operation of a light source. An exchange of a used-up cell is then possible without interrupting an operation of the surgical microscope.

Furthermore, in an exemplary embodiment, a plurality of semiconductor devices are provided as light sources, wherein these emit light in different wavelengths ranges, respectively. Light of different colour of the individual light sources is then superposed in such a manner that a field for surgery is illuminated by superposed light, a colour of which approximates that of white light agreeable to the surgeon.

Such a superposition can be effected such that it takes place at the field for surgery only, for instance by having sources of different colour emit their light directly to the field for surgery. In an alternative exemplary embodiment, however, a light mixer for generation of a superposition is provided, wherein the light mixer provides a light reflecting geometry, wherein at least a part of the light generated by the light sources is reflected once or more.

In an exemplary embodiment, the light mixer takes the form of a light guide which is disposed around at least a part of the circumference of the objective lens of the surgical microscope.

In a further exemplary embodiment, a semiconductor device is provided, which emits light and emits at least a portion of this light onto a phosphor (luminophor), which transforms incident light into light of a certain colour by luminescence, which can then be emitted onto the field for surgery. The semiconductor device may be, for instance, a light emitting diode emitting light in the ultraviolet, light of which is incident on a layer of a phosphor, which may contain one or more phosphors such that light emitted by this layer leaves an impression of about white colour. Equally, it is possible that the semiconductor may be a light emitting diode which emits blue light. A portion of this blue light may be used for illuminating the field for surgery, whereas a different portion of this light is incident on a layer of a phosphor, which is configured such that it transforms blue light into red or yellow light, for instance, which is equally used for illuminating the field for surgery. The light emitted by the blue LED and the light emitted by the phosphor can also be mixed in accordance with techniques described above in order to obtain an illumination light of the field for surgery which is about white and as homogeneous as possible.

Apart from the embodiment with a semiconductor device as the light source it is possible to use an organic device, such as an organic light emitting diode (OLED), or a light emitting polymer (LEP).

According to a further embodiment of the present invention, the light emitted by the light emitter is introduced into the surgical microscope from an outside, for instance by means of a light guide, whilst in addition, a photocell is provided on the surgical microscope, onto which a portion of the light supplied to the surgical microscope is incident, in order to generate current for operating one or more current consuming components of the surgical microscope by means of an optoelectrical process. It is then possible to do without a current supply lead conventionally disposed along the arms of the stand and, thereby, to reduce the remaining forces generated by the conventional current lead.

In an exemplary embodiment, a beam splitter is provided, through which light supplied to the light emitter passes in order to split the portion of light off which is then directed onto the photocell. In a further exemplary embodiment, the beam splitter is wavelength-selective and effects a splitting function substantially only for a range of wavelengths of the light supplied, which range is of no significant importance to the illumination of the field for surgery.

According to a further embodiment of the present invention, a device powered by electric current is disposed on the surgical microscope, and the surgical microscopy system comprises a power supply for operating this device. Herein, the power supply for leading current to or from the surgical microscope, respectively, comprises an electrically insulated wire each, which wires are separate from one another and extend as separate wires inbetween two attachment portions on different arms of the stand of a pair of arms pivotally connected to each other.

In contrast to a pair of wires of a current supply lead which is conventionally firmly fixed together, a wire separate from another wire provides lower remaining forces, similar to what has been described above in relation to the supply of light by two separate light guides.

In an exemplary embodiment, the two wires are a "twisted pair", i.e. mutually twisted wires.

According to a further embodiment, the power supply comprises an AC generator, an induction emitter supplied without operating power by the alternator, the induction emitter being attached to a first arm of the stand, and an induction receiver, the induction receiver being mounted to a second arm of the stand such as to face the induction emitter and to be movable relative thereto, the second arm being pivotally connected to the first arm. The induction emitter then supplies operating power to the device which is driven by electrical current.

In accordance with a further embodiment, the power supply comprises a contact rail disposed on a first arm and a sliding contact disposed adjacent to the first contact rail, wherein the sliding contact is disposed on a different arm which is pivotally connected to the first arm. Herein, a current lead, which, for instance, bridges a joint between adjacent arms of the stand is rendered redundant altogether.

According to a further embodiment, at least a mechanically supporting component of an arm of the stand is configured to form part of a current path to or from the device powered by electrical current. This current path provided by the mechanically supporting component of the arm of the stand then replaces a conventionally provided current lead such that remaining forces exerted by this conventional current lead no longer exist.

According to a further embodiment, the current required for operation of the current consuming device is not provided by a current lead, but the required energy is transmitted by wireless transmission, for which purpose a radiation emitter is provided at a distance from the surgical microscope and a corresponding radiation receiver is provided on the surgical microscope. The receiver transforms the received radiation into an electrical current for operation of the device. The energy radiation may be, for instance, infrared radiation, microwave radiation or laser radiation.

In an exemplary embodiment, the emitter has a distinctly directional characteristic, which is adjustable in dependence of the position of the surgical microscope such that a large portion of the radiation energy emitted by the radiation emitter is incident on the radiation receiver.

According to a further embodiment, the power supply comprises an electrochemical cell disposed on a base of the stand, such as an accumulator or the like.

This is particularly advantageous when the base of the stand is configured to be placed on the floor of the room and therefore is supposed to have an increased weight for securing a stability of the stand. In these embodiments, power supply leads for supplying energy to the surgical microscopy system are not necessary, which facilitates the work of the surgeon who conventionally has to pay attention not to stumble over leads running across the floor of the operation theatre.

As an alternative solution for this problem, induction emitters attached to the floor or disposed in the floor are provided which work in cooperation with an induction receiver disposed on the base of the stand for transmitting energy to the surgical microscopy system.

In accordance with a further embodiment of the present invention, the surgical microscope is provided with a data acquisition unit or a data display unit, and the surgical microscopy system comprises a data transmission system for transmitting data to the data display unit or away from the acquisition unit. In contrast to a coaxial cable or the like conventionally used for these purposes a pair of wires is used, which wires are separate from one another. These wires extend separately from one another between two attachment portions or points, which attachment portions are disposed on a pair of pivotally connected arms of the stand, similarly to the embodiment described above in connection with the description of the pair of current supply wires. Also, the possibilities of a "twisted pair" of wires, of the use of contact rails and sliding contacts, as well as using a mechanically supporting component of arms of the stand for electrical data transmission, which have been described in connection with the current supply, are equally applicable here.

In accordance with a further embodiment, a transmission system comprises a data modulator and an induction transmitter powered by the data modulating unit. The induction transmitter is mounted on a first arm of the stand and the induction receiver mounted to a second arm of the stand in such a manner that it faces the induction transmitter and is movable with respect thereto, wherein the at least first arm and the second arm are pivotally connected, and wherein a data demodulator is coupled to the induction receiver.

If the surgical microscope comprises a data display unit, in an exemplary embodiment, a data demodulator is coupled to the data display unit. This coupling may extend over further arms of the stand wherein these, in turn, comprise pairs of induction transmitter and induction receiver.

If the surgical microscope comprises a data acquisition unit, in an exemplary embodiment, the data acquisition unit is coupled to the data modulator, wherein here, also, the coupling may extend over several arms of the stand, pairs of which comprise induction transmitters and induction receivers facing each other.

According to a further embodiment, data transmission is provided by a light guide, which is disposed along the arms of the stand. Due to the high bandwidth of the data transmission through light guides it is possible to save a plurality of conventional data transmission lines.

Furthermore, it is possible to have a light guide for data transmission together with a light guide for supplying illumination to the surgical microscope. For instance, a light source can be modulated for data transmission and this modulation can be detected at the surgical microscope, or light for its transmission can be coupled into the light guide for supplying the illumination light coupled out again at the surgical microscope. In an exemplary embodiment, light for data transmission is coupled into merely one glass fibre or a few glass fibres of light guides for transmission of the illumination light and that only light of this one or few glass fibres is demodulated at the other end of the light guide.

According to further embodiments, wave guides for providing electromagnetic radiation are disposed on arms of the stand and are connected or jointed, at locations where adjacent arms of the stand are pivotally connected, without there being inacceptably high transmission losses.

In accordance with a further embodiment, an optocoupler is provided for transmission of data from one arm of the stand to an adjacent arm of the stand. Components of the optocoupler, i.e. transmitter and receiver, are then movable relative to each other, together with the pivotally connected arms of the stand, without being too detrimental to a transmission quality.

According to a further embodiment, transmission is provided in a wireless form, by having a transmitter or/and receiver for data disposed on the surgical microscope and a corresponding receiver or transmitter disposed at a distance from the surgical microscope. Between transmitter and receiver, a transmission is carried out electromagnetically through wireless transmission. Wireless transmission processes according to at least one of blue tooth standard, IEEE 802.11b standard, and hyperLAN standard are used in exemplary embodiments.

According to a further embodiment, the data are compressed before their transmission by the transmitter and decompressed after their receipt. This enables transmission of large amounts of data in the form of image data in a satisfactory manner. Compression according to a process is used in an exemplary embodiment, wherein conventionally only information with regard to a part of an image to be transmitted is transmitted, which part has changed in comparison to a previously transmitted image. An example for such a process is known as MPEG4 which provides a further advantage in that it allows to use one of a substantially static background and a dynamic foreground.

Such a compression process is typically particularly effective for images taken through a surgical microscope, since the scenario in a field for surgery changes only very slowly in practice and then only in small areas of the field for surgery where the surgeon carries out manipulations with his instruments.

BRIEF DESCRIPTION OF THE DRAWINGS

The forgoing as well as other advantageous features of the invention will be more apparent from the following detailed description of exemplary embodiments of the invention with reference to the accompanying drawings, wherein.

DETAILED DESCRIPTION OF EXEMPLARY EMBODIMENTS

Figure 1:
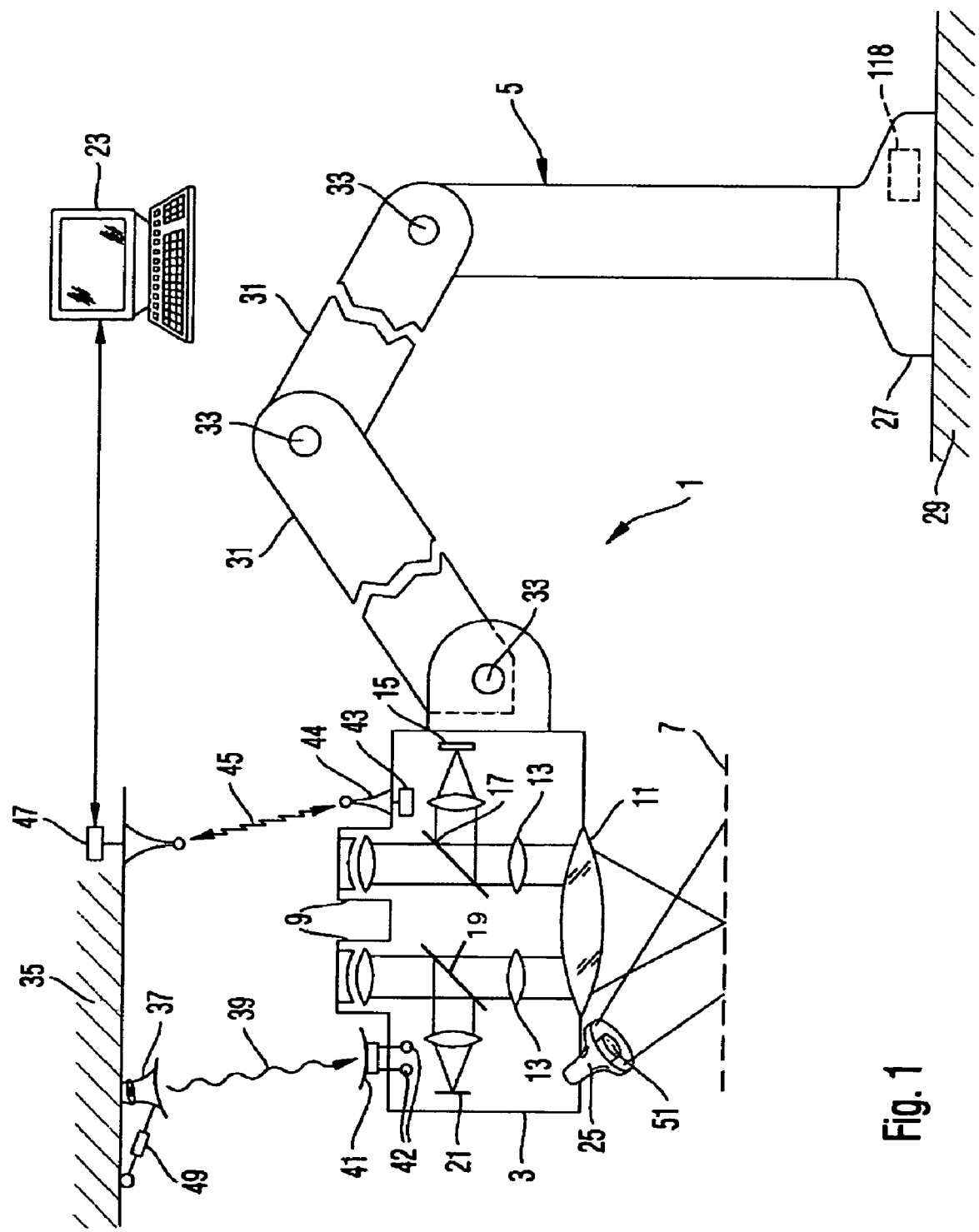
FIG. 1 shows a schematic representation of an embodiment of a surgical microscopy system.

FIG. 1 shows a microscopy system 1 comprising a surgical microscope 3 and a stand 5 holding the surgical microscope 3.

The surgical microscope 3 provides an enlarged image of the field for surgery 7 to a surgeon who can view the field for surgery 7 through two oculars 9. The microscope 3 comprises objective lens 11 (symbolically depicted), and two zoom systems 13 associated with oculars 9 (depicted in a symbolic manner). A camera 15 is provided to take a picture of the field for surgery 7, which picture is decoupled from a path of one of the oculars by means of a semireflecting mirror 17. In a beam path of the other ocular, a further semireflecting mirror 19 is provided, however, this mirror 19 serves to couple in an image displayed by LC display unit 21 and generated by computer 23, which image may be a display of numerical values of measured data points or the like, into a beam path of this ocular such that the surgeon sees a superposition of the field for surgery 7 and the image generated by display 21 in the ocular. Apart from objective lens 11, an illumination assembly 25 is provided in order to illuminate the field for surgery 7.

The stand 5 comprises a base 27 of the stand for arranging stand 5 on the floor 29 of an operating theatre as well as a plurality of arms 31 of the stand which are pivotally connected by means of joints 33. An end of the chain of arms 31 of the stand thus formed is connected via a joint 33 to the base 27 of the stand and its other end is connected to a further joint 33 and thus to the surgical microscope 3. Stand 5 is a so-called balanced out stand, which means that forces exerted onto stand 5 by the burden to be carried, namely the surgical microscope 3 which forces attempt to move arms 31 and joints 33 of the stand are compensated for by the mechanics of stand 5 in such a way that the surgical microscope 3 is substantially suspended freely in the room and can be moved to a different position in the room by moving it by hand.

On a ceiling 35 of the operating theatre, a microwave transmitter 37 is provided which emits a microwave beam 39 towards the surgical microscope 3, in particular in such a manner that the microwave beam is incident on a microwave receiver 41 disposed on surgical microscope 3. Microwave receiver 41 transforms the received microwaves into electrical energy and provides an operating voltage for the electrically powered components of the surgical microscope 3 at the electrical connectors 42. These electrically powered components comprise the illumination assembly 25, the camera 15 and the display 21. Furthermore, microwaves are supplied by microwave receiver 41 to a sender/receiver 43 having a sending/receiving antenna 44. The sender/receiver 43 communicates in a wireless manner 45 with a corresponding sender/receiver 47 which is mounted to the ceiling 35 of the operating theatre. The distance for wireless transmissions serves for transmission of images taken by camera 15 of the field for surgery 7 to computer 23 which analyses these pictures and/or stores them into an archive.

It is also possible to transmit these pictures to a plurality of additional observers.

Furthermore, the distance 45 for wireless transmission serves to transmit data generated by computer 23 which are displayed by display 21. Furthermore, a signal is transmitted from surgical microscope 3 across the distance 45 for wireless transmission to the computer 23 which signal represents the microwave power received by microwave receiver 41. In dependence of the signal, the computer 23 operates an actuator 49 configured to effect swivelling of microwave sender 37 in such a manner that a microwave power received by receiver 41 is substantially a maximum.

The surgical microscopy system 1 depicted in FIG. 1 does not have any leads which are led along the arms 31 of the stand towards the surgical microscope 3:

The light for illumination of the field for surgery 7 is generated in the illumination assembly 25 by means of a light source 51 which may be, for instance, a halogen lamp or a white-light LED, in particular disposed in immediate vicinity of the surgical microscope 3. Thus, provision of light by means of conventional light guides is not necessary; the electrical power necessary for operation of the electrically powered components is supplied to the surgical microscope 3 by microwave beam 39, and therefore, a conventional electrical power supply is not necessary; data transmission from surgical microscope 3 to computer 23 and from computer 23 to the surgical microscope 3 is effected across a distance 45 for wireless transmission, which is why conventional data lines are rendered redundant in the surgical microscopy system 1 as well.

The white-light LED mentioned above may be a device which comprises several separate LEDs which each emit light of different colours which, after a suitable mixing of light results in about white light. Furthermore, the white-light LED can be a device which comprises a light source, which light source emits light of a certain wavelength or a certain wavelength band which is at least partially incident on a phosphor which transforms this light into light of a different wavelength band so that a suitable superposition of different kinds of light results again in white-light. The light source may be, for instance, a blue light source the light of which is incident on a phosphor which transforms the blue light into about yellow light. Mixture of the blue light of the light source and the yellow light of the phosphor then results in about white light which may be used for illumination of the field for surgery. It is also possible that the light source generates light from an ultraviolet wavelength band which is incident on a suitable phosphor which transforms the ultraviolet light into visible light of such a wavelength distribution that about a white colour impression is generated. For this purpose the phosphors can be a mixture of several single phosphors.

In the following, alternative embodiments of the surgical microscopy system described with reference to FIG. 1 will be described in more detail. Herein, components which correspond to components of the system of FIG. 1 in terms of their configuration and their function, are referred to using the same reference numerals, with an additional letter added for purposes of differentiation. Reference is also made to the entire description above. In the following Figures, merely parts of the surgical microscopy system are depicted as far as they are necessary for illustrating the different approaches for avoiding leads along the arms of the stand or for reducing remaining forces introduced by the leads.

Figure 2:
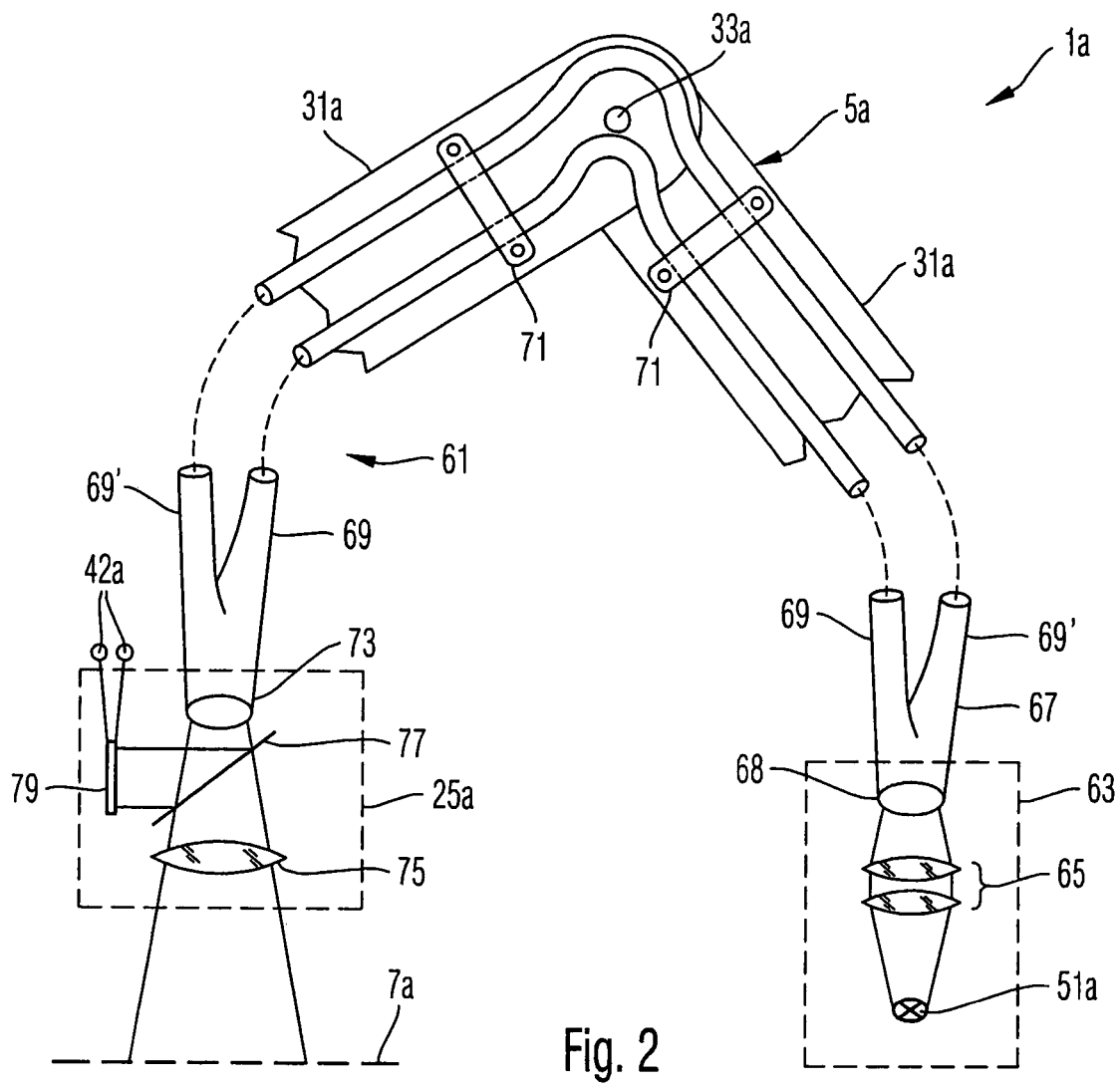
FIG. 2 shows a schematic partial illustration of a further embodiment of a surgical microscopy system.

A surgical microscopy system 1a depicted partially in FIG. 2 comprises a plurality of pivotally connected Lamp 51a generates, apart from light necessary for illuminating the field for surgery 7a with white light, also light which is close to the edge or outside of the visible spectrum. In a beam path between the light emitting end 73 of light guide arrangement 61 and the collimation optic 75a semireflecting mirror 77 is disposed which allows light from a central range of the visible spectrum to substantially pass and at least partially reflects light which has a wavelength underneath and/or above the central range. The reflected light is incident onto a photocell 79 which transforms the light energy into electrical energy and provides a supply voltage at electrical connectors 42a to electrically powered components of the surgical microscope. That way, electrical energy required for the operation of these components is generated in the immediate vicinity of the surgical microscope and does not need to be supplied via electrical leads which would need to be led along arms 31a of the stand.

Figure 3:
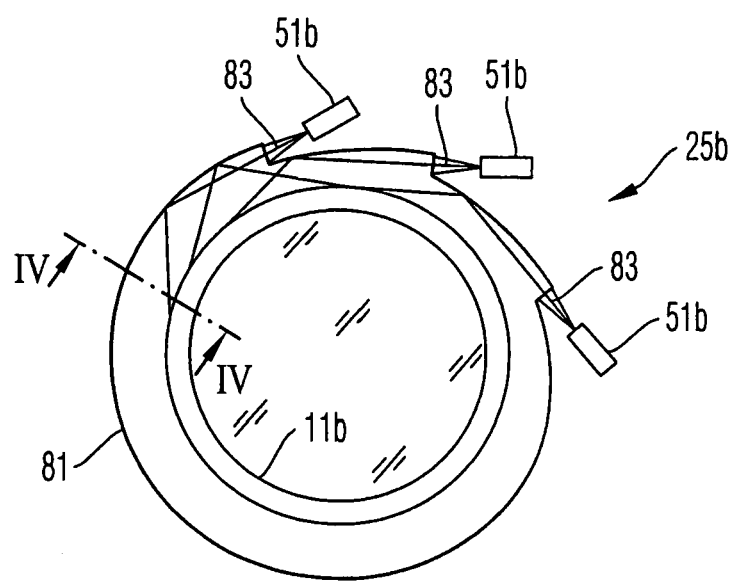
FIG. 3 shows a partial illustration of a detail of a further embodiment of a surgical microscopy system.
Figure 4:
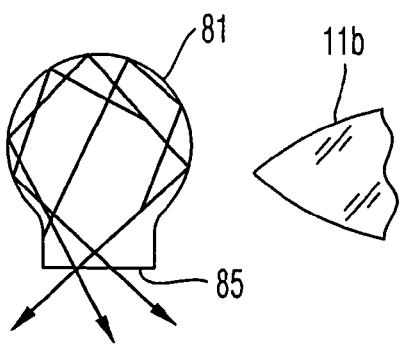
FIG. 4 shows a sectional view along the line IV—IV in FIG. 3.

An illumination assembly 25b is schematically depicted in FIGS. 3 and 4. Illumination assembly 25b comprises three light diodes 51b as a source of radiation, a first light diode emitting red light, a second diode emitting yellow light and a third diode emitting blue light. Light emitted by light diodes 51b, respectively, is coupled into a light mixer 81 in the form of a Perspex ring 81, at in-coupling areas 83. After being coupled into the Perspex ring the light beams are subjected to total reflection at the surface of ring 81 and are thus distributed in a direction of a circumference of the ring 81 and simultaneously mixed with respect to the colours. As apparent from the cross sectional view according to FIG. 4, ring 81 has a substantially round cross section, but also has an appendix with a planar light exiting face 85 through which light beams having a sufficiently high angle of incidence onto arms 31a of the stand. Light to be emitted by an illumination assembly 25a for illumination of the field for surgery mounted on the surgical microscope carried by stand 5a is led to the illumination assembly via an arrangement of light guides 61. The light is generated by means of a halogen lamp 51a or a xenon lamp in a radiation source 63 which is attached to a base of stand 5a. A collimator 65 couples light emitted by lamp 51a into a light guide 67 on an in-coupling end 68 thereof. Light guide 67 has a round cross section at its in-coupling end 68 and then divides into two parts 69 and 69' having round cross sections each. However, cross sections of parts 69 and 69' are of only half the size as compared to the cross section at the in-coupling end. The two light guides 69, 69' are led together along arms 31 of the stand up to the surgical microscope and are attached at respective points or portions of attachment by means of cable fastener 71 or the like. These are disposed on each arm 31 on the stand having a distance to a joint 33a for connecting two adjacent pivotally connected arms of the stand. In the surgical microscope both light guides 69 and 69' are reunited into a common light guide, an emitting end 73 of light guide arrangement 61 having the same round cross section as the in-coupling end 68.

The light emitting end 73 is arranged in illumination assembly 25a and light exiting from the light emitting end 73 is formed by a collimation optic 75 in order to illuminate the field for surgery 7a.

The division of light guide for leading light to the surgical microscope into two light guides has the advantage that the two light guides 69, 69' exert smaller remaining forces onto joints 33a than would be the case for a single light guide having the same cross sectional area as the two light guides 69, 69' together. surface 85 may exit and be emitted in the direction of the field for surgery. The ring is disposed radially outward of objective lens 11b.

Providing light necessary for illumination of the field for surgery by means of light diodes has the advantage that these diodes are able to generate light of a respective colour or white light with a relatively good efficiency and therefore require relatively little electrical energy. This renders the conventionally used light guides for providing light to the surgical microscope unnecessary. Electrical energy required for operation of the light diode 51b can be supplied to the surgical microscope by means of electrical leads, which may be provided anyway. However, those electrical leads are not required if the energy is transmitted to the surgical microscope by wireless means as described above with reference to FIG. 1.

Furthermore, generating light by means of light diodes disposed on the surgical microscope permits to use an electrochemical cell for supplying power, which electrochemical cell is disposed on the surgical microscope itself as described in the following with reference to FIG. 5.

Figure 5:
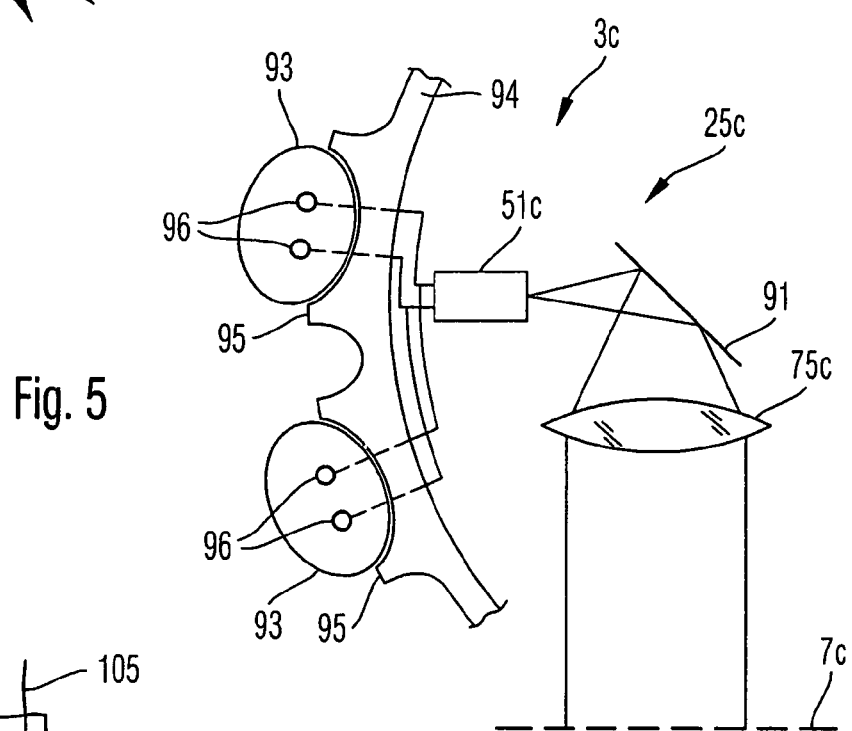
FIG. 5 shows a schematic partial illustration of a further embodiment of a surgical microscopy system.

In FIG. 5, surgical microscope 3c comprises an illumination arrangement 25c comprising a light diode as a source of radiation 51c which diode emits ultraviolet light. This ultraviolet light is incident onto a fluorescent screen 91 and is transformed into visible light by this screen, a spectral composition of this light being such that is perceived as a relatively good white light. Light generated by the fluorescent screen 91 is collimated by collimator 75c and emitted in the direction of a field for surgery 7c. Light diode 51c is supplied with energy from fuel cells 93 electrically arranged in parallel, which fuel cells are attached to an outside of a microscope housing 94 by means of cell holders 95. Fuel cells 93 are each removable from the housing and are disposed so as to engage with contacts 96 when mounted to the holders 95. Thus, they can transmit the generated electrical power to the power supply of the surgical microscope and supply power to light diode 51c as well as further power consuming components of the microscope.

One of cells 93 can be removed from the microscope when it is used-up and replaced by a freshly reloaded cell whilst the other cell ensures constant energy supply to the microscope.

As an alternative to the fuel cells described above, other electrochemical cells such as NiCd-accumulators or nickel-metal-hydrid-accumulators may be used.

Figure 6:
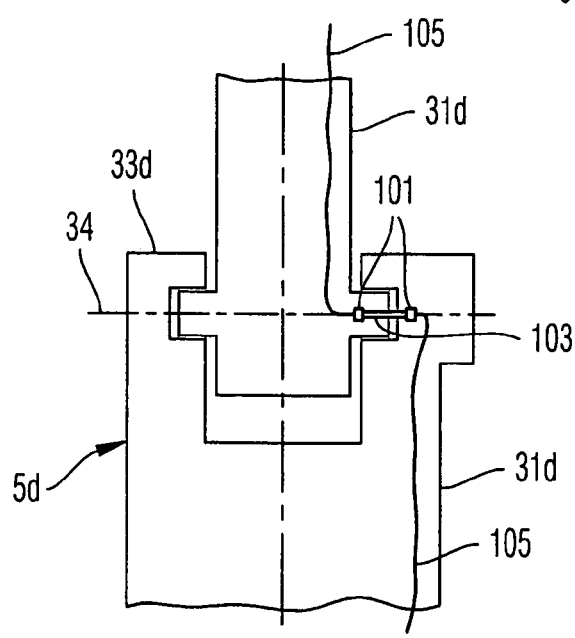
FIG. 6

In FIG. 6 a further possibility for realizing data transmission to or away from a surgical microscope is illustrated.

Stand 5*d* comprises a plurality of arms 31*d* which are pivotally connected to each other by means of joints 33*d* and may be swivelled around corresponding swivelling axis 34. The data are transmitted in arms 31*d* of the stand via leads 105. However, in order to transmit data from one arm to an arm pivotally connected thereto, transmission of data is provided by means of an optocoupler 101 which is disposed on joint 33*d* such that a light distance 103 between the two optocouplers 101 is substantially disposed on the swivelling axis 34. This way no data transmission lines are to be provided which bridge the joint 33*d* between the arms 31*d* and, accordingly, no remaining forces generated by data transmission lines are exerted onto arms 31 of the stand.

Figure 7:
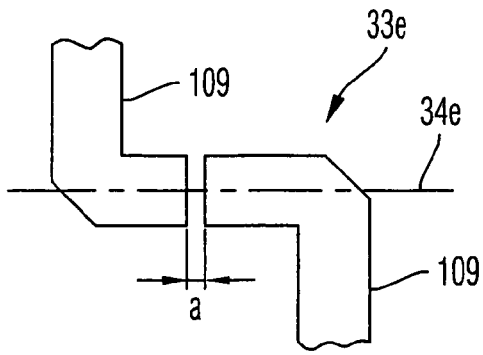
FIG. 7

In FIG. 7 a further embodiment of the data transmission system is depicted which is similar to the embodiment shown in FIG. 6.

Although, in this embodiment, wave guides 109 are used within arms of the stand. The data to be transmitted are modulated into electromagnetic waves which are led by wave guide 109. In an area of joint 33*e* between pivotally connected arms of the stand, wave guides 109 extend on a swivelling axis 34 of joint 33*e* towards each other such that only a sufficiently small gap "a" remains between them such that electromagnetic waves cross from one wave guide 109 into the other without too much loss.

Figure 8:
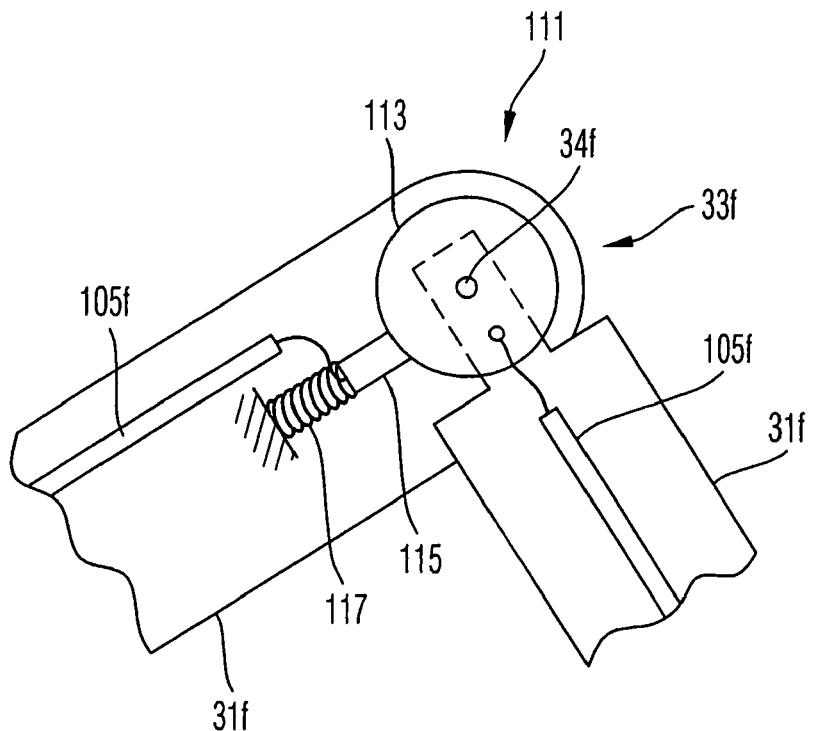
FIG. 8

A further embodiment for replacing an electrical cable bridging one of the joints between two arms of the stand, either for transmission of data or for power supply to the surgical microscope, is schematically depicted in FIG. 8.

Wires 105*f* are run within arms 31*f* of the stand. However, these wires do not run continuously from one arm 31*f* of the stand to the next. Rather, a slip ring assembly 111 is provided which has a round contact rail 113 attached to one arm 31*f* of the stand such that the centre of the circle is coincident with a swivelling axis 34*f* of joint 33*f*. At the other arm 31*f* of the stand a sliding contact 115 is engaged with a spring 117 such that a reliable contact is established between sliding contact 115 and contact rail 113. Sliding contact 115 and contact rail 113 are then electrically connected to the respective wires 105*f* run through the respective arms 31*f* of the stand.

A plurality of sliding ring arrangements of this kind may be provided at joints between adjacent arms of the stand in order to provide an electrical current or voltage transmission for a plurality of wires, which is free of remaining forces.

In another embodiment, a current path, which may be at ground potential, for instance, is provided by supporting components of arms 31*f* of the stand which are made of metal. In joint 33*f* the axis of the joint and bearings for the same also provide sufficient electrical contact for current and/or data transmission since they are in immediate mechanical engagement with each other.

Figure 10:
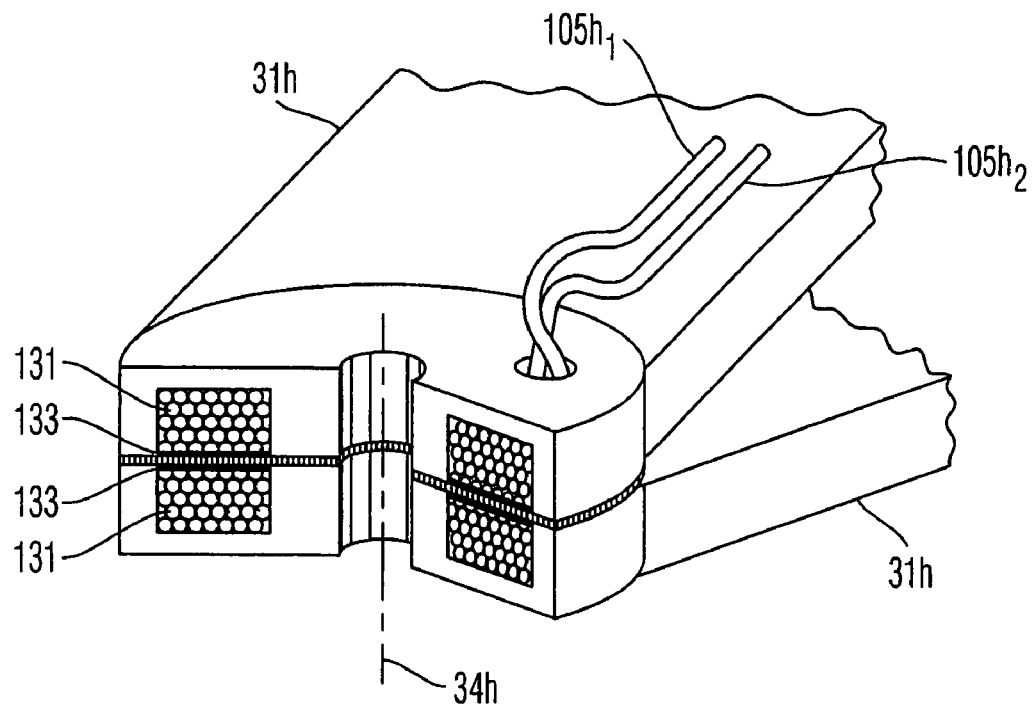
FIG. 10 shows a part of a stand with a detail of a data and current transmission system.
Figure 11:
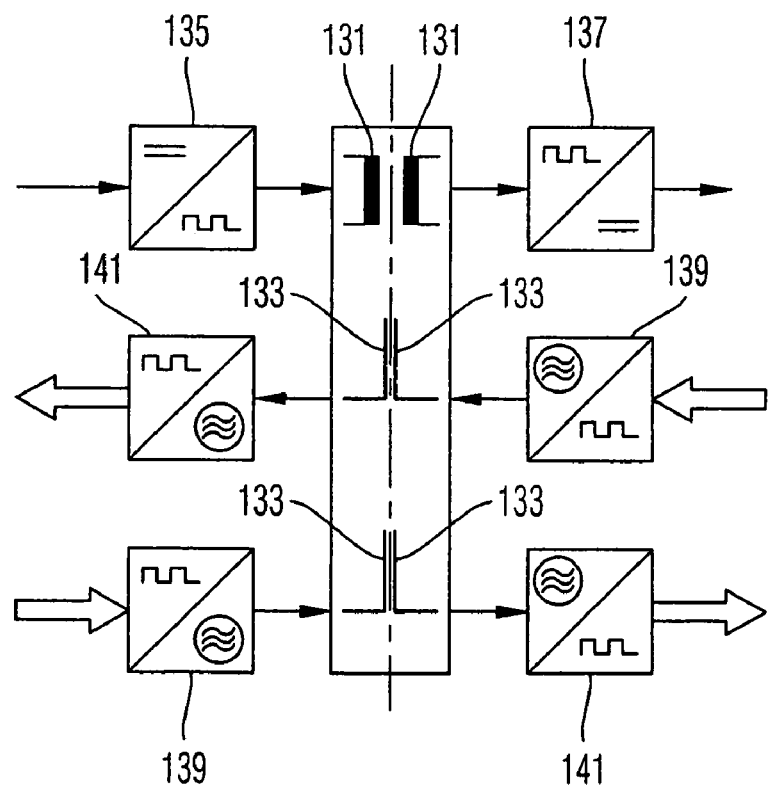
FIG. 11 shows a functional diagram of the data and current transmission system of FIG. 10.

FIGS. 10 and 11 explain a further embodiment for transmission of electrical power and data between adjacent arms of the stand.

FIG. 10 shows a perspective, cut open detail illustration of two arms 31*h* of the stand which are pivotally connected and may be swivelled around swivelling axis 34*h*. Current leads 105$h_1$ and a data line 105$h_2$ are run along arms 31*h* of the stand. For transmission of current or data, respectively, across the joint, each of the two arms 31*h* of the stand comprises a winding 131 which is concentric with respect to a swivelling axis 34*h*. The winding 131 is connected to the respective current lead 105$h_1$ and a flat antenna 133 which is concentric with respect to swivelling axis 34*h* which antenna is coupled to data line 105$h_2$.

The flat antennae 133 transmit the data without contact between the arms 31*h* of the stand and the windings 131 transmit electrical power inductively between arms 31*h* of the stand. This way, a powerful transmission of electrical power and data between the two arms 31*h* of the stand is realized without the need for leading corresponding leads from one arm of the stand to the other.

FIG. 11 shows a detailed diagram of connections of the transmission of electrical power and data between the two arms 31*h* of the stand depicted in FIG. 10. An inverter 135 is disposed on a side of one of the arms 31*h* of the stand, to which inverter electrical power is supplied as DC and which transforms the electrical power into an AC, which is supplied to the winding 131 of arm 31*h* of the stand. The winding 131 of the other arm of the stand receives the electrical power and supplies this electrical power in the form of AC to a converter 137 which, in turn, transforms this into direct current.

The transmission of data via the antennae 133 is bi-directional, with a data modulator 139 being provided on each of the two arms of the stand. Data are supplied digitally to the data modulator and the data modulator transforms these into an AC voltage suitable for transmission by the antennae 133. Correspondingly, a corresponding demodulator 141 is provided on each arm 31*h* of the stand, which demodulator transforms the AC voltage received by the corresponding antennae 133 into corresponding digital data again.

Herein, it is also possible to transmit electrical power and data across a chain of a plurality of joints wherein inverters or converters, respectively, and modulators or demodulators, respectively, may be disposed at the ends of the chain of arms of the stand only, and the antennae 133 or the windings 131, respectively, are connected via suitable leads along the arms of the stand within the chain.

The system comprising inverter 135, converter 137, modulator 139, demodulator 141, windings 131 and antennae 133 may be commercially obtained under the product name "COMBITRANS" from the company MST Aerospace GmbH, Eupener Str. 50, 50933 Köln, Germany.

Figure 9:
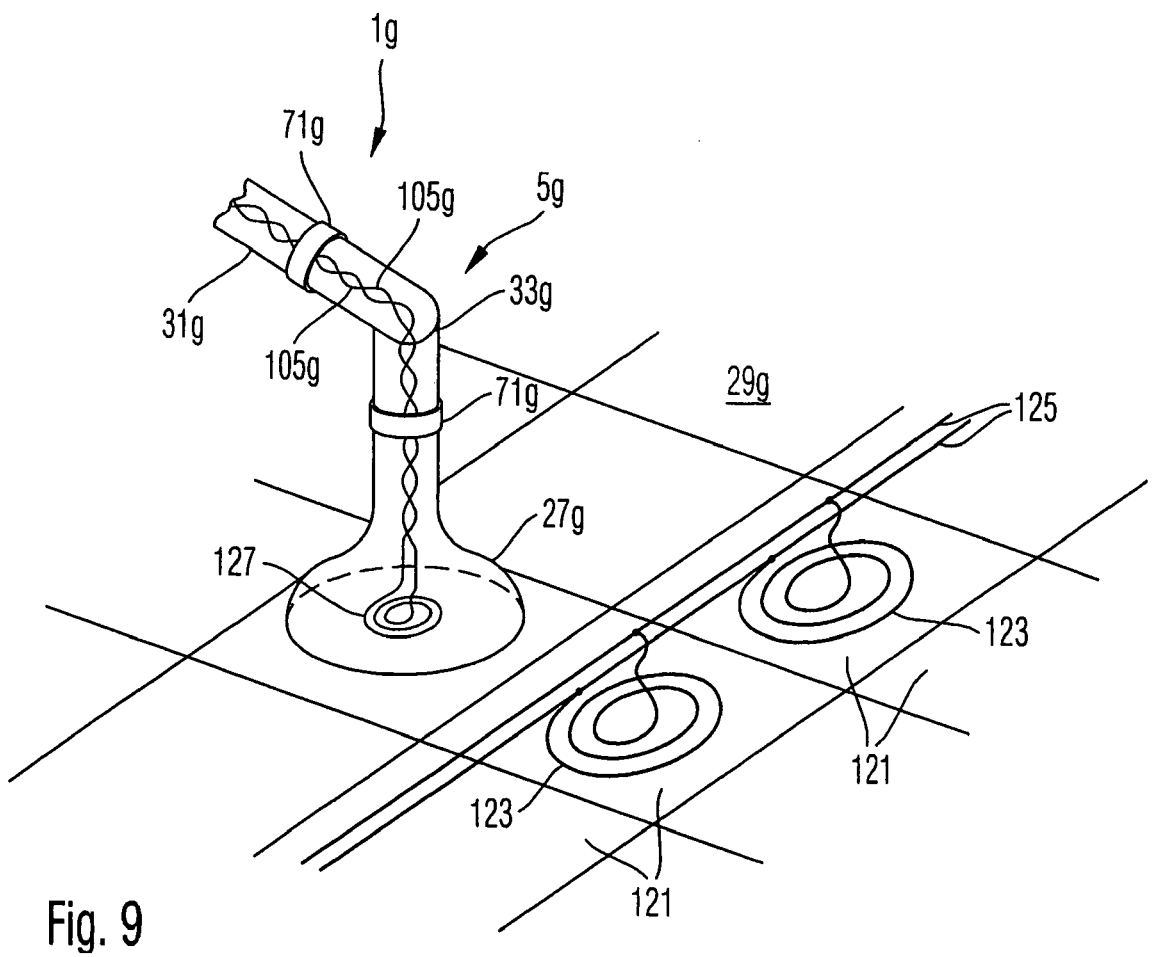
FIG. 9 each show a partially schematic illustration of a further embodiment of a surgical microscopy system.

FIG. 9 explains a possibility for supplying electrical energy to a surgical microscopy system 1*g* from outside without having to have electrical leads on a floor 29*g* of an operating theatre.

For this purpose, floor 29*g* comprises a field of rectangular, mutually adjacent floor tiles 121, wherein in each of the floor tiles 121 an induction coil 123 is disposed (depicted in an manner in FIG. 9 for merely two corners of a floor tile). An electrical AC current is supplied to induction coils 123 via supply leads 125, which several induction coils 123 are electrically connected to in parallel, respectively.

In a base 27*g* of a stand 5*g* of the surgical microscopy system 1*g*, a further induction coil 127, corresponding to induction coils 123, is provided into which an electrical energy is coupled when the base 27*g* of the stand is disposed in an area of one of the induction coils 123 of the floor tiles 121.

The electrical energy coupled into induction coil 127 of the stand 5*g* is led along arms of the stand 31*g* by means of two separate, i.e. un-connected, wires 105*g* which are in the form of a "twisted wire pair". The pair of wires 105*g* is attached to arms 31*g* of the stand by means of belt bands 71*g* which are disposed at a distance from joint 33*g* of the stand 5g. Such loosely twisted wires 105g provide relatively smaller remaining forces against swivelling of joints 33g, as compared to connected wires.

Such twisted pairs of wire or several twisted wires cannot only be used for transmitting electrical energy for purposes of power supply to the surgical microscope but also for data transmission to the microscope or away from the microscope.

Although not depicted in FIG. 9, it is also possible to selectively supply AC current only to those induction coils 123 in the floor tiles 121, in the proximity of which base 27g of the stand is disposed.

In FIG. 1, as an alternative embodiment for a current supply of a surgical microscope including a stand, a battery 118 is indicated by dotted lines, which battery is disposed in a base of the stand. This battery serves to supply the stand and the surgical microscope with operating energy. The battery can be a rechargeable battery. For recharging the battery, energy is supplied thereto by means of a cable, which may be connected to the stand. During operation, however, it is not necessary for a current supply cable to be disposed on the floor of the operating theatre for supplying energy to the surgical microscope.

Furthermore, it is possible that the battery 118 may be removed from the base of the stand such that a discharged battery can be exchanged. In such an embodiment, in particular two batteries 118 are provided in order to maintain the operation of the surgical microscope during the exchange of one of the batteries.

The possibility of mixing light of different colours depicted with reference to FIGS. 3 and 4 has the character of an independent invention and is therefore not restricted to a microscopy system with a stand. Mixing light may be used in any kind of surgical microscope. Accordingly, a surgical microscope according to the present invention comprises an objective lens for receiving light from an object field and generating an enlarged image of the object field therefrom, and a plurality of light sources which generate light of different colours, respectively, which is used for illumination of the object field. In particular, a light mixer is provided. The light mixer, in particular, at least partially surrounds the objective lens. The light mixer may be a light guide into which light of different colours is coupled. In particular, the light guide emits light along a long side of the same in the direction of an object plane. Particularly, the light guide is a ring-shaped closed light guide.

In summary, the invention has a surgical microscopy 1 as a starting point, comprising a surgical microscope 3 and a stand 5 with a stand base 27 and several pivotally connected arms 31 of the stand, one of which carries the surgical microscope, wherein pivotally connected members of the stand are movable relative to each other such that the surgical microscope may be displaced relative to a base of the stand and wherein a lead conventionally led along arms of the stand is replaced by two or more leads carrying out the function thereof together.

Furthermore, it is provided that data and/or energy is transmitted to the surgical microscope 39, 45 in a wireless manner.

The present invention has been described by way of exemplary embodiments to which it is not limited. Variations and modifications will occur to those skilled in the art without departing from the scope of the present invention as recited in the appended claims and equivalents thereof.

What is claimed is:

1. A surgical microscopy system, comprising:
a surgical microscope; and
a stand comprising a base and a plurality of pivotally connected arms, the surgical microscope being mounted to one of the arms, wherein the pivotally connected arms are arranged to be movable with respect to each other such that the surgical microscope is movable relative to the base;
wherein the surgical microscope comprises a device powered by electrical current and wherein the surgical microscope comprises a power supply of the device,
the power supply comprising a contact rail disposed on a first arm and a sliding contact disposed adjacent to the contact rail, wherein the sliding contact is disposed on a second arm and wherein the second arm is pivotally connected to the first arm.

2. A surgical microscopy system, comprising:
a surgical microscope;
a stand comprising a base and a plurality of pivotally connected arms, the surgical microscope being mounted to one of the arms, wherein the pivotally connected arms are arranged to be movable with respect to each other such that the surgical microscope is movable relative to the base;
wherein the surgical microscope comprises a device powered by electrical current and wherein the surgical microscope comprises a power supply of the device, and
wherein a mechanically supporting component of the stand is configured to form part of a current path to or from the device powered by electrical current, said mechanically supporting component of said stand includes a portion of one of said pivotally connected arms and further wherein at least one of current and data flow through said portion.

3. The surgical microscopy system of claim 2, further comprising:
at least one light emitter, mounted on the surgical microscope, for illuminating a field for surgery,
wherein the at least one light emitter comprises at least one of a light generating semiconductor device mounted on the surgical microscope, an organic light generating device mounted on the surgical microscope, and a light emitting polymer device mounted on the surgical microscope.

4. The surgical microscopy system of claim 3, wherein the organic light generating device is an organic light emitting diode.

5. The surgical microscopy system of claim 3, further comprising at least one electrochemical cell mounted on the surgical microscope, the at least one electrochemical cell being provided for generating electrical power and supplying electrical power to the at least one light emitter.

6. The surgical microscopy system of claim 5, comprising a pair of electrochemical cells which are independently removable from the surgical microscope.

7. The surgical microscopy system of claim 5, wherein the electrochemical cell comprises a fuel cell.

8. The surgical microscopy system of claim 3, comprising at least two semiconductor devices, wherein a first semiconductor device generates light of a wavelength range at least partially different from at least a wavelength range of light generated by a second semiconductor device.

9. The surgical microscopy system of claim 8, wherein the light emitter comprises a light mixer configured such that the light generated by the at least two semiconductor devices is reflected a plurality of times before being emitted.

10. The surgical microscopy system of claim 9, wherein the light mixer comprises a light guide, which is at least partially disposed around an objective lens of the surgical microscope, and wherein the light for illuminating the field for surgery is emitted by the light guide.

11. A surgical microscopy system, comprising:

a surgical microscope;

a stand comprising a base and a plurality of pivotally connected arms, the surgical microscope being mounted to one of the arms, wherein the pivotally connected arms are arranged to be movable with respect to each other such that the surgical microscope is movable relative to the base;

wherein the surgical microscope comprises a device powered by electrical current and wherein the surgical microscope comprises a power supply of the device, and wherein the base of the stand is adapted to be disposed on a floor of a room, wherein the base comprises an induction receiver to be used in combination with at least one induction transmitter disposed on or in the floor of the room, and wherein the induction receiver supplies the device powered by the electrical current with operating power.

12. A surgical microscopy system, comprising:

a surgical microscope;

a stand comprising a base and a plurality of pivotally connected arms, the surgical microscope being mounted to one of the arms, wherein the pivotally connected arms are arranged to be movable with respect to each other such that the surgical microscope is movable relative to the base;

wherein the surgical microscope comprises a device powered by electrical current and wherein the surgical microscope comprises a power supply of the device, and wherein a mechanically supporting component of the stand is configured to form part of a current path to or from the device powered by electrical current, wherein said power supply further comprises a contact rail disposed on a first arm and a sliding contact disposed adjacent to the contact rail, wherein the sliding contact is disposed on a second arm and wherein the second arm is pivotally connected to the first arm.

13. A surgical microscopy system, comprising:

a surgical microscope;

a stand comprising a base and a plurality of pivotally connected arms, the surgical microscope being mounted to one of the arms, wherein the pivotally connected arms are arranged to be movable with respect to each other such that the surgical microscope is movable relative to the base;

wherein the surgical microscope comprises a device powered by electrical current and wherein the surgical microscope comprises a power supply of the device, and wherein a mechanically supporting component of the stand is configured to form part of a current path to or from the device powered by electrical current, wherein the base of the stand is adapted to be disposed on a floor of a room, wherein the base comprises an induction receiver to be used in combination with at least one induction transmitter disposed on or in the floor of the room, and wherein the induction receiver supplies the device powered by the electrical current with operating power.

* * * * *

UNITED STATES PATENT AND TRADEMARK OFFICE
CERTIFICATE OF CORRECTION

PATENT NO. : 7,248,402 B2
APPLICATION NO. : 10/730021
DATED : July 24, 2007
INVENTOR(S) : Andreas Obrebski et al.

It is certified that error appears in the above-identified patent and that said Letters Patent is hereby corrected as shown below:

On the Title Page, Item -56-, under "OTHER PUBLICATIONS", change "Kontaktiose Drehubertrager" to --Kontaktlose Drehübertrager--.

Column 9, line 30, change "75*a*" to --75, a--.

Column 9, line 25, move the entire section beginning with "Lamp" and ending at column 9, line 58 at "onto" to column 10, line 24, immediately before "surface".

Column 12, line 44, change "Eupener Str. 50, 50933 KöIn," to --Eupener Str. 50, 50933, Köln--.

Signed and Sealed this

Fifteenth Day of April, 2008

JON W. DUDAS
*Director of the United States Patent and Trademark Office*